US007993829B2

(12) United States Patent
Friedman et al.

(10) Patent No.: US 7,993,829 B2
(45) Date of Patent: Aug. 9, 2011

(54) HPRP4S MODIFIERS OF THE P53 PATHWAY AND METHODS OF USE

(75) Inventors: Lori Friedman, San Francisco, CA (US); Gregory D. Plowman, San Carlos, CA (US); Tak Hung, Foster City, CA (US); Helen Francis-Lang, San Francisco, CA (US); Danix Li, San Francisco, CA (US); Roel P. Funke, South San Francisco, CA (US); Michael Costa, San Francisco, CA (US)

(73) Assignee: Exelixis Inc., South San Francisco, CA (US)

( * ) Notice: Subject to any disclaimer, the term of this patent is extended or adjusted under 35 U.S.C. 154(b) by 0 days.

(21) Appl. No.: 11/627,831

(22) Filed: Jan. 26, 2007

(65) Prior Publication Data

US 2007/0160539 A1     Jul. 12, 2007

Related U.S. Application Data

(63) Continuation of application No. 10/211,133, filed on Aug. 2, 2002, now abandoned.

(60) Provisional application No. 60/310,362, filed on Aug. 6, 2001, provisional application No. 60/357,501, filed on Feb. 15, 2002.

(51) Int. Cl.
*C12Q 1/68* (2006.01)

(52) U.S. Cl. ............................................... 435/6; 435/4

(58) Field of Classification Search ........................ None
See application file for complete search history.

(56) References Cited

U.S. PATENT DOCUMENTS 6,165,461 A    12/2000   Cobb et al.

OTHER PUBLICATIONS

Groβ et al, Nucleic Acids Research, 1997, 25:1028-1035.*
Huang et al (Biochemical and Biophysical Research Communications, 2000, 271:456-463).*
Colman (J of Cell Science, 1990, 97:399-409).*
Summerton (Biochemica et Biophysica Acta, 1999, 1489:141-158).*
Schumacher et al (Current Biology, 2001, 11:1722-1727).*
Bowie et al (Science, 1990, 257:1306-1310).*
Burgess et al (J of Cell Bio. 111:2129-2138, 1990).*
Scott et al (Nature Genetics, 1999, 21:440-443).*
Kaji et al (Molecular Carcinogenesis, 2003, 37:138-148).*
Harris and Levine (Oncogene, 2005, 24:2899-2908).*
Kojima et al (Journal of Biological Chemistry, 2001, 276:32247-32256).*
Kojima, Tatsuya et al.: "Cloning of Human PRP4 Reveals Interaction with Clk1," The Journal of Biological Chemistry, vol. 276, No. 34, Issue of Aug. 24, pp. 32247-32256 (2001).
Colwill et al.: "The CLK/Sry protein kinase phosphorylates SR splicing factors and regulates their intranuclear distribution," The EMBO Journal, 1996, vol. 15, No. 2, pp. 265-275.
Gobert et al.: "Modulation of DNA Topoisomerase I activity by p53," Biochemistry, 1996, vol. 35, pp. 5778-5786.
Papoutsopoulou et al.: "SR protein-specific kinase 1 is highly expressed in testis and phosphorylates protamine 1," Nucleic Acids Research, 1999, vol. 27, No. 14, pp. 2972-2980.
Nayler et al.: "Characterization and comparison of four serine-and arginine-rich (SR) protein kinases," Biochemistry Journal, 1997, vol. 326, pp. 693-700.
T. Kojima et al.: "*Homo sapiens* serine/theronine-protein kinase (PRP4) mRNA, complete cds," GenBank GI No. 14571505, Aug. 21, 2001.
T. Gross et al.: "*Homo sapiens* serine/theronine-protein kinase PRP4 homolog (PRP4), mRNA," Genbank GI No. 17999534, May 16, 2002.
NCBI Annotation Project, *Homo sapiens* serine/theronine-protein kinase PRP4 homolog (PRP4), mRNA, GenBank GI No. 14714402, Jul. 12, 2001.
Strausberg, R. et al. "*Homo sapiens*, serine/theronine-protein kinase PRP4 homolog, clone IMAGE: 3943395, mRNA," Genbank GI No. 1399461, Jul. 2, 1996.
Luetzelberger, M. et al.: "Human serine/theronine-protein kinase PRP4h (PRP4h) mRNA, complete cds," Genbank GI No. 1399461, Jul. 2, 1996.

* cited by examiner

*Primary Examiner* — Laura B Goddard
(74) *Attorney, Agent, or Firm* — McDonnell Boehnen Hulbert & Berghoff LLP

(57) ABSTRACT

Human hPRP4 genes are identified as modulators of the p53 pathway, and thus are therapeutic targets for disorders associated with defective p53 function. Methods for identifying modulators of p53, comprising screening for agents that modulate the activity of hPRP4 are provided.

Figure 1:
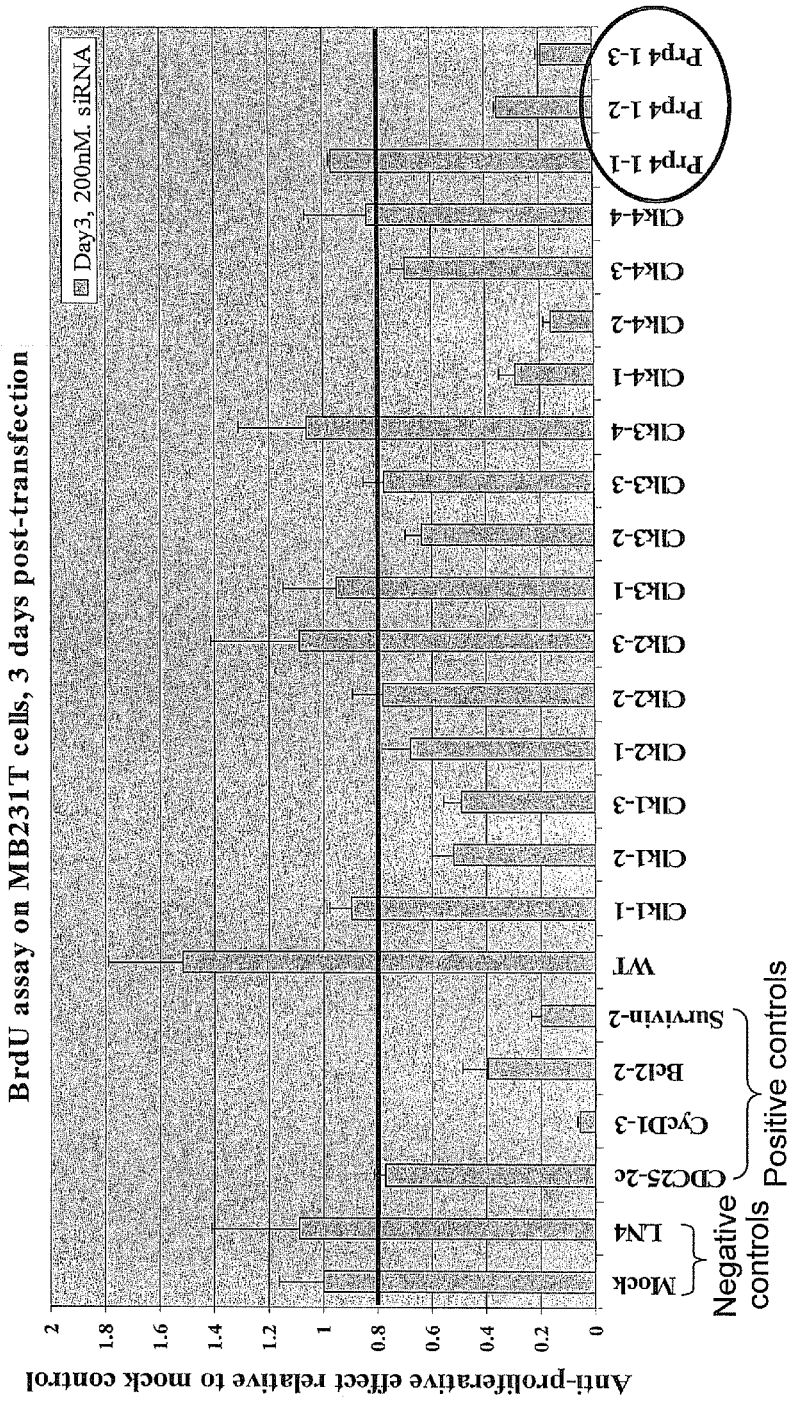
Figure 2:
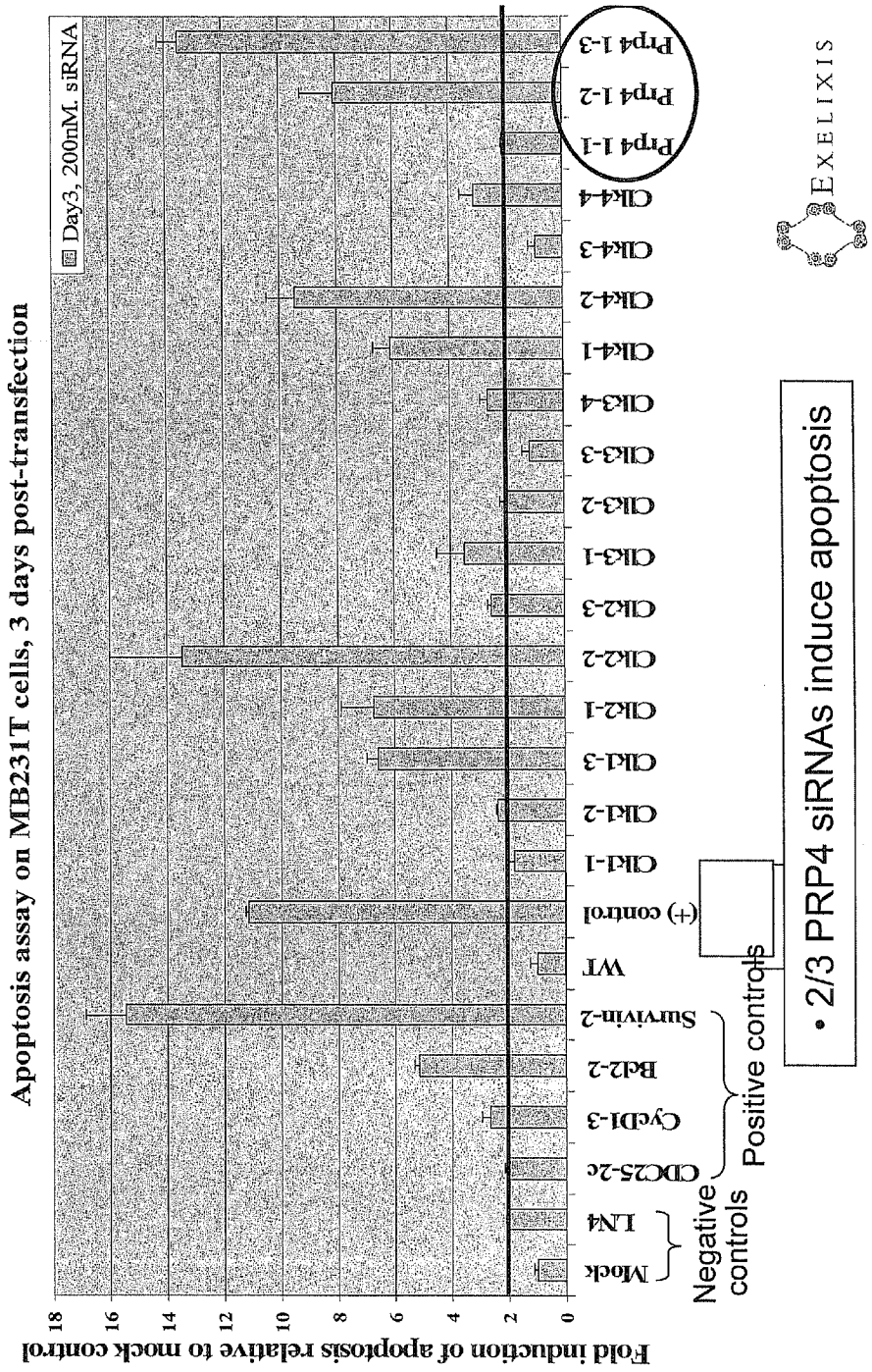

10 Claims, 2 Drawing Sheets ized. The assay system may be cell-based or

SEQUENCE LISTING

```
<160> NUMBER OF SEQ ID NOS: 7

<210> SEQ ID NO 1
<211> LENGTH: 3024
<212> TYPE: DNA
<213> ORGANISM: Homo sapiens

<400> SEQUENCE: 1
atggccgccg cggagaccca gtcgctacgg gagcagccag agatggaaga tgctaattct      60
gaaaagagta taaatgaaga aaatggagaa gtatcagaag accagtctca aaataagcac     120
agtcgtcaca aaaaaagaa gcataaacac agaagtaaac ataagaaaca taacattcc      180 tcagaagaag acaaggataa aaaacataaa cataagcata aacataagaa acacaaaaga     240
aaagaggtta ttgatgcttc tgataaagag ggtatgtctc cagcaaaaag aactaaactt     300
gatgatttag ctttgctaga agacttggaa aaacagagag ccttgattaa ggccgaactt     360
gataatgagt taatggaagg aaaggtccag tctggtatgg ggctcatttt gcaaggttat     420
gagtctggct ctgaagaaga gggggaaatt catgaaaagg caagaaatgg aaataggtct     480
agtactagat cttcaagtac aaaggggaaa cttgaacttg tggacaataa aattactaca     540
aagaaacgaa gtaaaagcag atccaaagaa cggactagac ataggtctga taaaaagaaa     600
agtaaggggg gtattgaaat cgttaaagag aaaacaacta ggagcaagtc aaggagagg      660 aaaaaatcta aaagcccatc caaagaagt aagtctcaag atcaagcaag gaaatcaaaa      720
tcccctaccc ttagaaggcg atctcaagag aaaattggta aggccagatc tcctactgat     780
gataaggtta aaattgaaga taaaagtaaa tcaaagata ggaaaaaatc cccaattata      840
aatgaaagta gaagtcgcga tcgaggtaaa aaatccagat ccccagttga tttaagaggt     900
aaatccaaag acagaaggtc acggtccaaa gagagaaaat caaaacggtc tgaaactgat     960
aagaaaaaga agccaattaa atctccctct aaagatgctt catctgggaa agaaaatagg    1020
tcacccagca gaagacctgg tcgtagtcct aaaagaagaa gtttgtctcc aaaaccacgt    1080
gataaatcaa gaagaagcag gtctccactt ttgaatgata aagatctaa gcagagcaaa    1140 tcccctcgc ggacactgtc tcctgggaga agagccaaga gccgatcctt agaaagaaaa    1200
cgacgagaac cagagaggag acgactttct tctccaagaa cacgacctcg agatgatatc    1260
ctcagtagac gtgaaagatc aaaagatgcc agccccatca atagatggtc tccaacccga    1320
agaagaagta gatctcccat tagaaggagg tctcgttccc cactcagacg tagcaggtct    1380
ccaagaagaa gaagcagatc tcctcggaga agggacagag gtcggaggag cagatcacgc    1440
ttgcgaaggc ggtctcgatc acgcggtggt cgtagacgaa ggagcagaag caaagtaaag    1500
```

| | |
|---|---|
| gaagataaat ttaaaggaag tctttctgaa ggaatgaaag ttgagcagga atcttcgtct | 1560 |
| gatgataacc ttgaagactt tgatgtagag gaagaagatg aagaagccct aatagaacag | 1620 |
| agaagaatcc aaaggcaggc aattgttcag aaatataaat accttgctga agatagcaac | 1680 |
| atgtctgtgc catctgaacc aagcagcccc cagagcagta cgagaacacg atcaccatct | 1740 |
| ccagatgaca ttctggagcg agtagctgct gatgttaaag agtatgaacg ggaaaatgtt | 1800 |
| gatacatttg aggcctcagt gaaagccaag cataatctaa tgacagttga acagaataat | 1860 |
| ggttcatctc agaagaagtt gttggcacct gatatgttta cagaatctga tgatatgttt | 1920 |
| gctgcgtatt ttgatagtgc tcgtcttcgg gccgctggca ttggaaaaga tttcaaagag | 1980 |
| aatcccaacc tcagagataa ctggaccgat gcagaaggct attatcgtgt gaacataggt | 2040 |
| gaagtcctag ataaacgtta caatgtgtat ggctacactg gcaaggtgt attcagtaat | 2100 |
| gttgtacgag ccagagataa tgcaagagcc aaccaagaag tggctgtaaa gatcatcaga | 2160 |
| aacaatgagc tcatgcaaaa gactggttta aaagaattag agttcttgaa aaacttaat | 2220 |
| gatgctgatc ctgatgacaa atttcattgt ctgagactct tcaggcactt ctatcacaag | 2280 |
| cagcatcttt gtctggtatt cgagcctctc agcatgaact tacgagaggt gttaaaaaaa | 2340 |
| tatggtaaag atgttggtct tcatattaaa gctgtaagat cctatagtca gcagttgttc | 2400 |
| ctggcattga aactccttaa aagatgcaat atcctacatg cagatatcaa ccagacaat | 2460 |
| atcctggtta atgaatccaa aactatttta aagctttgcg attttgggtc ggcttcacat | 2520 |
| gttgcggata atgacataac accttatctt gtcagtagat tttatcgtgc tcctgaaatc | 2580 |
| attataggta aaagctatga ctatggtata gatatgtggt ctgtaggttg cacctttatac | 2640 |
| gaactctata ctggaaaaat tttattccct ggcaaaacca ataaccatat gctgaagctt | 2700 |
| gcaatggatc tcaaaggaaa gatgccaaat aagatgattc gaaaaggtgt gttcaaagat | 2760 |
| cagcattttg atcaaaatct caacttcatg tacatagaag ttgataaagt aacagagagg | 2820 |
| gagaaagtta ctgttatgag caccattaat ccaactaagg acctgttggc tgacttgatt | 2880 |
| gggtgccaga gacttcctga agaccaacgt aagaaagtac accagctaaa ggacttgttg | 2940 |
| gaccagattc tgatgttgga cccagctaaa cgaattagca tcaaccaggc cctacagcac | 3000 |
| gccttcatcc aggaaaaaat ttaa | 3024 |

```
<210> SEQ ID NO 2
<211> LENGTH: 3202
<212> TYPE: DNA
<213> ORGANISM: Homo sapiens

<400> SEQUENCE: 2
```

| | |
|---|---|
| cttcccctac cctccaccgt ccgggagccg ccgccaccgc cgccgaggag tcaggaagtt | 60 |
| caagatggcc gccgcggaga cccagtcgct acgggagcag ccagagatgg aagatgctaa | 120 |
| ttctgaaaag agtataaatg aagaaaatgg agaagtatca gaagaccagt ctcaaaataa | 180 |
| gcacagtcgt cacaaaaaaa agaagcataa acacagaagt aaacataaga acataaaca | 240 |
| ttcctcagaa gaagacaagg ataaaaaaca taaacataag cataaacata gaaacacaa | 300 |
| aagaaaagag gttattgatg cttctgataa agagggtatg tctccagcaa aagaactaa | 360 |
| acttgatgat ttagctttgc tagaagactt ggaaaaacag agagccttga ttaaggccga | 420 |
| acttgataat gagttaatgg aaggaaaggt ccagtctggt atgggctca ttttgcaagg | 480 |
| ttatgagtct ggctctgaag aagaggggga aattcatgaa aaggcaagaa atggaaatag | 540 |
| gtctagtact agatcttcaa gtacaaaggg gaaacttgaa cttgtggaca ataaaattac | 600 |

```
tacaaagaaa cgaagtaaaa gcagatccaa agaacggact agacataggt ctgataaaaa    660
gaaaagtaag gggggtattg aaatcgttaa agagaaaaca actaggagca agtcaaagga    720
gaggaaaaaa tctaaaagcc catccaaaag aagtaagtct caagatcaag caaggaaatc    780
aaaatcccct acccttagaa ggcgatctca agagaaaatt ggtaaggcca gatctcctac    840
tgatgataag gttaaaattg aagataaaag taaatcaaaa gataggaaaa aatccccaat    900
tataaatgaa agtagaagtc gcgatcgagg taaaaaatcc agatccccag ttgatttaag    960
aggtaaatcc aaagacagaa ggtcacggtc caaagagaga aaatcaaaac ggtctgaaac   1020
tgataaagaa aagaagccaa ttaaatctcc ctctaaagat gcttcatctg ggaaagaaaa   1080
taggtcaccc agcagaagac ctggtcgtag tcctaaaaga agaagtttgt ctccaaaacc   1140
acgtgataaa tcaagaagaa gcaggtctcc acttttgaat gatagaagat ctaagcagag   1200
caaatccccc tcgcggacac tgtctcctgg gagaagagcc aagagccgat ccttagaaag   1260
aaaacgacga gaaccagaga ggagacgact ttcttctcca agaacacgac ctcgagatga   1320
tatcctcagt agacgtgaaa gatcaaaaga tgccagcccc atcaatagat ggtctccaac   1380
ccgaagaaga agtagatctc ccattagaag gaggtctcgt tccccactca gacgtagcag   1440
gtctccaaga agaagaagca gatctcctcg gagaagggac agaggtcgga ggagcagatc   1500
acgcttgcga aggcggtctc gatcacgcgg tggtcgtaga cgaaggagca gaagcaaagt   1560
aaaggaagat aaatttaaag gaagtctttc tgaaggaatg aaagttgagc aggaatcttc   1620
gtctgatgat aaccttgaag actttgatgt agaggaagaa gatgaagaag ccctaataga   1680
acagagaaga atccaaaggc aggcaattgt tcagaaatat aaataccttg ctgaagatag   1740
caacatgtct gtgccatctg aaccaagcag cccccagagc agtacgagaa cacgatcacc   1800
atctccagat gacattctgg agcgagtagc tgctgatgtt aaagagtatg aacgggaaaa   1860
tgttgataca tttgaggcct cagtgaaagc caagcataat ctaatgacag ttaacagaa    1920 taatggttca tctcagaaga agttgttggc acctgatatg tttacagaat ctgatgatat   1980
gtttgctgcg tattttgata gtgctcgtct tcgggccgct ggcattggaa agatttcaa    2040 agagaatccc aacctcagag ataactggac cgatgcagaa ggctattatc gtgtgaacat   2100
aggtgaagtc ctagataaac gttacaatgt gtatggctac actgggcaag gtgtattcag   2160
taatgttgta cgagccagag ataatgcaag agccaaccaa gaagtggctg taaagatcat   2220
cagaaacaat gagctcatgc aaaagactgg tttaaaagaa ttagagttct tgaaaaaact   2280
taatgatgct gatcctgatg acaaatttca ttgtctgaga ctcttcaggc acttctatca   2340
caagcagcat ctttgtctgg tattcgagcc tctcagcatg aacttacgag aggtgttaaa   2400
aaaatatggt aaagatgttg gtcttcatat taaagctgta agatcctata gtcagcagtt   2460
gttcctggca ttgaaactcc ttaaaagatg caatatccta catgcagata tcaagccaga   2520
caatatcctg gttaatgaat ccaaaactat tttaaagctt tgcgattttg ggtcggcttc   2580
acatgttgcg gataatgaca taacacctta tcttgtcagt agattttatc gtgctcctga   2640
aatcattata ggtaaaagct atgactatgg tatagatatg tggtctgtag ttgcaccctt   2700
atacgaactc tatactggaa aaattttatt ccctggcaaa accaataacc atatgctgaa   2760
gcttgcaatg gatctcaaag gaaagatgcc aaataagatg attcgaaaag gtgtgttcaa   2820
agatcagcat tttgatcaaa atctcaactt catgtacata gaagttgata agtaacaga    2880 gagggagaaa gttactgtta tgagcaccat taatccaact aaggacctgt tggctgactt   2940
gattgggtgc cagagacttc ctgaagacca acgtaagaaa gtacaccagc taaaggactt   3000
```

```
gttggaccag attctgatgt tggacccagc taaacgaatt agcatcaacc aggccctaca    3060
gcacgccttc atccaggaaa aaatttaaac aagatgaaga aactccaagg gtttgagtaa    3120
atacaaagac tgaagaaatt tcacagcagt ttattaatgt atataaactt ataaatattt    3180
ctccagcaaa tttgaggaag ca                                             3202

<210> SEQ ID NO 3
<211> LENGTH: 1719
<212> TYPE: DNA
<213> ORGANISM: Homo sapiens

<400> SEQUENCE: 3
ggtcggagga gcagatcacg cttgcgaagg cggtctcgat cacgcggtgg tcgtagacga      60
aggagcagaa gcaaagtaaa ggaagataaa tttaaaggaa gtctttctga aggaatgaaa     120
gttgagcagg aatcttcgtc tgatgataac cttgaagact ttgatgtaga ggaagaagat     180
gaagaagccc taatagaaca gagaagaatc caaaggcagg caattgttca gaaatataaa     240
taccttgctg aagatagcaa catgtctgtg ccatctgaac caagcagccc ccagagcagt     300
acgagaacac gatcaccatc tccagatgac attctggagc gagtagctgc tgatgttaaa     360
gagtatgaac gggaaaatgt tgatacattt gaggcctcag tgaaagccaa gcataatcta     420
atgacagttg aacagaataa tggttcatct cagaagaagt tgttggcacc tgatatgttt     480
acagaatctg atgatatgtt tgctgcgtat tttgatagtg ctcgtcttcg ggccgctggc     540
attggaaaag atttcaaaga gaatcccaac ctcagagata actggaccga tgcagaaggc     600
tattatcgtg tgaacatagg tgaagtccta gataaacgtt acaatgtgta tggctacact     660
gggcaaggtg tattcagtaa tgttgtacga gccagagata atgcaagagc caaccaagaa     720
gtggctgtaa agatcatcag aaacaatgag ctcatgcaaa agactggttt aaaagaatta     780
gagttccttg aaaaacttaa tgatgctgat cctgatgaca aatttcattg tctgagactc     840
ttcaggcact tctatcacaa gcagcatctt tgtctggtat tcgagcctct cagcatgaac     900
ttacgagagg tgttaaaaaa atatggtaaa gatgttggtc ttcatattaa agctgtaaga     960
tcctatagtc agcagttgtt cctggcattg aaactcctta aaagatgcaa tatcctacat    1020
gcagatatca agccagacaa tatcctggtt aatgaatcca aaactatttt aaagctttgc    1080
gattttgggt cggcttcaca tgttgcggat aatgacataa cacctatct tgtcagtaga    1140 ttttatcgtg ctcctgaaat cattataggt aaaagctatg actatggtat agatatgtgg    1200
tctgtaggtt gcaccttata cgaactctat actggaaaaa tttattccc tggcaaaacc    1260 aataaccata tgctgaagct tgcaatggat ctcaaaggaa agatgccaaa taagatgatt    1320
cgaaaaggtg tgttcaaaga tcagcatttt gatcaaaatc tcaacttcat gtacatagaa    1380
gttgataaag taacagagag ggagaaagtt actgttatga gcaccattaa tccaactaag    1440
gacctgttgg ctgacttgat tgggtgccag agacttcctg aagaccaacg taagaaagta    1500
caccagctaa aggacttgtt ggaccagatt ctgatgttgg acccagctaa acgaattagc    1560
atcaaccagg ccctacagca cgccttcatc caggaaaaaa tttaaacaag atgaagaaac    1620
tccaagggtt tgagtaaata caaagactga agaaatttca cagcagttta ttaatgtata    1680
taaacttata aatatttctc cagcaaattt gaggaagca                           1719

<210> SEQ ID NO 4
<211> LENGTH: 2393
<212> TYPE: DNA
<213> ORGANISM: Homo sapiens
```

```
<400> SEQUENCE: 4
ggcacgaggc tcagtagacg tgaaagatca aaagatgcca gcccatcaat agatggtctc      60
caacccgaag aagaagtaga tctcccatta gaaggaggtc tcgttcccca ctcagacgta     120
gcaggtctcc aagaagaaga agcagatctc ctcggagaag ggacagaggt cggaggagca     180
gatcacgctt gcgaaggcgg tctcgatcac gcggtggtcg tagacgaagg agcagaagca     240
aagtaaagga agataaattt aaaggaagtc tttctgaagg aatgaaagtt gagcaggaat     300
cttcgtctga tgataacctt gaagactttg atgtagagga agaagatgaa gaagccctaa     360
tagaacagag aagaatccaa aggcaggcaa ttgttcagaa atataaatac cttgctgaag     420
atagcaacat gtctgtgcca tctgaaccaa gcagccccca gagcagtacg agaacacgat     480
caccatctcc agatgacatt ctggagcgag tagctgctga tgttaaagag tatgaacggg     540
aaaatgttga tacatttgag gcctcagtga aagccaagca taatctaatg acagttgaac     600
agaataatgg ttcatctcag aagaagttgt tggcacctga tatgtttaca gaatctgatg     660
atatgtttgc tgcgtatttt gatagtgctc gtcttcgggc cgctggcatt ggaaaagatt     720
tcaaagagaa tcccaacctc agagataact ggaccgatgc agaaggctat tatcgtgtga     780
acataggtga agtcctagat aaacgttaca atgtgtatgg ctacactggg caaggtgtat     840
tcagtaatgt tgtacgagcc agagataatg caagagccaa ccaagaagtg gctgtaaaga     900
tcatcagaaa caatgagctc atgcaaaaga ctggtttaaa agaattagag ttcttgaaaa     960
aacttaatga tgctgatcct gatgacaaat tcattgtct gagactcttc aggcacttct    1020
atcacaagca gcatctttgt ctggtattcg agcctctcag catgaactta cgagaggtgt    1080
taaaaaaata tggtaaagat gttggtcttc atattaaagc tgtaagatcc tatagtcagc    1140
agttgttcct ggcattgaaa ctccttaaaa gatgcaatat cctacatgca gatatcaagc    1200
cagacaatat cctggttaat gaatccaaaa ctattttaaa gctttgcgat tttgggtcgg    1260
cttcacatgt tgcggataat gacataacac cttatcttgt cagtagattt tatcgtgctc    1320
ctgaaatcat tataggtaaa agctatgact atggtataga tatgtggtct gtaggttgca    1380
ccttatacga actctatact ggaaaaattt tattccctgg caaaaccaat aaccatatgc    1440
tgaagcttgc aatggatctc aaaggaaaga tgccaaataa gatgattcga aaaggtgtgt    1500
tcaaagatca gcattttgat caaaatctca acttcatgta catagaagtt gataaagtaa    1560
cagagaggga gaaagttact gttatgagca ccattaatcc aactaaggac tgttggctg    1620 acttgattgg gtgccagaga cttcctgaag accaacgtaa gaaagtacac cagctaaagg    1680
acttgttgga ccagattctg atgttggacc cagctaaacg aattagcatc aaccaggccc    1740
tacagcacgc cttcatccag gaaaaaattt aaacaagatg aagaaactcc aagggtttga    1800
gtgtgtgtgt gcaggccaca gcagcatgcc cttggtgtag tcagtgccga aagggggtctg    1860 ttccttcttg agcctgcctg cagggatggt ctcctttttaa agcaggttgt gtgcagcatt    1920
cagtacactg aaggcataaa ccttccactc ttgaacaaag cagctgcttt ttaaaagcga    1980
gaaaaaggaa aacggggcac aggccattcg acgccttctc caagggtct gatttgctga    2040 gacaccagct tcaccttctt aacaaggcac ctaattacaa caagcatgca cattttggtg    2100
cattcaagaa tggaaaatca gaatagcagc attgattctt ctggtgcagc tcagtggaag    2160
atgatgacaa ccagaagaca tgagctaagg gtaagggact gttctgaaga acctttccat    2220
ttagtgatca agatatggaa gctgatttct gaaaatgctc agtgtgtact ctaattattt    2280
atggtaccat ttgaattgta acttgcattt tagcagtgca tgtttctaat tgacttactg    2340
```

| ggaaactgaa taaaatatgc ctcttattat caaaaaaaaa aaaaaaaaaa aaa | 2393 |

<210> SEQ ID NO 5
<211> LENGTH: 1718
<212> TYPE: DNA
<213> ORGANISM: Homo sapiens

<400> SEQUENCE: 5

| ggtcggagga gcagatcacg cttgcgaagg cggtctcgat cacgcggtgg tcgtagacga | 60 |
| aggagcagaa gcaaagtaag gaagataaat ttaaaggaag tctttctgaa ggaatgaaag | 120 |
| ttgagcagga atcttcgtct gatgataacc ttgaagactt tgatgtagag gaagaagatg | 180 |
| aagaagccct aatagaacag agaagaatcc aaaggcaggc aattgttcag aaatataaat | 240 |
| accttgctga agatagcaac atgtctgtgc catctgaacc aagcagcccc cagagcagta | 300 |
| cgagaacacg atcaccatct ccagatgaca ttctggagcg agtagctgct gatgttaaag | 360 |
| agtatgaacg ggaaaatgtt gatacatttg aggcctcagt gaaagccaag cataatctaa | 420 |
| tgacagttga acagaataat ggttcatctc agaagaagtt gttggcacct gatatgttta | 480 |
| cagaatctga tgatatgttt gctgcgtatt ttgatagtgc tcgtcttcgg gccgctggca | 540 |
| ttggaaaaga tttcaaagag aatcccaacc tcagagataa ctggaccgat gcagaaggct | 600 |
| attatcgtgt gaacataggt gaagtcctag ataaacgtta caatgtgtat ggctacactg | 660 |
| ggcaaggtgt attcagtaat gttgtacgag ccagagataa tgcaagagcc aaccaagaag | 720 |
| tggctgtaaa gatcatcaga acaatgagc tcatgcaaaa gactggttta aaagaattag | 780 |
| agttcttgaa aaagcttaat gatgctgatc ctgatgacaa atttcattgt ctgagactct | 840 |
| tcaggcactt ctatcacaag cagcatcttt gtctggtatt cgagcctctc agcatgaact | 900 |
| tacgagaggt gttaaaaaaa tatggtaaag atgttggtct tcatattaaa gctgtaagat | 960 |
| cctatagtca gcagttgttc ctggcattga aactccttaa aagatgcaat atcctacatg | 1020 |
| cagatatcaa gccagacaat atcctggtta tgaatccaa aactatttta aagctttgcg | 1080 |
| attttgggtc ggcttcacat gttgcggata tgcatacaac accttatctt gtcagtagat | 1140 |
| tttatcgtgc tcctgaaatc attataggta aaagctatga ctatggtata gatatgtggt | 1200 |
| ctgtaggttg caccttatac gaactctata ctggaaaaat tttattccct ggcaaaacca | 1260 |
| ataaccatat gctgaagctt gcaatggatc tcaaaggaaa gatgccaaat aagatgattc | 1320 |
| gaaaaggtgt gttcaaagat cagcattttg atcaaaatct caacttcatg tacatagaag | 1380 |
| ttgataaagt aacagagagg gagaaagtta ctgttatgag caccattaat ccaactaagg | 1440 |
| acctgttggc tgacttgatt gggtgccaga gacttcctga agaccaacgt aagaaagtac | 1500 |
| accagctaaa ggacttgttg gaccagattc tgatgttgga cccagctaaa cgaattagca | 1560 |
| tcaaccaggc cctacagcac gccttcatcc aggaaaaaat ttaaacaaga tgaagaaact | 1620 |
| ccaagggttt gagtaaatac aaagatgaag aaatttcaca gcagtttcat taatgtatat | 1680 |
| aaacttataa atatttctcc agcaaatttg aggaagca | 1718 |

<210> SEQ ID NO 6
<211> LENGTH: 3024
<212> TYPE: DNA
<213> ORGANISM: Homo sapiens

<400> SEQUENCE: 6

| atggccgccg cggagaccca gtcgctacgg gagcagccag agatggaaga tgctaattct | 60 |
| gaaaagagta taaatgaaga aaatggagaa gtatcagaag accagtctca aaataagcac | 120 |

```
agtcgtcaca aaaaaaagaa gcataaacac agaagtaaac ataagaaaca taaacattcc    180
tcagaagaag acaaggataa aaaacataaa cataagcata aacataagaa acacaaaaga    240
aaagaggtta ttgatgcttc tgataaagag ggtatgtctc cagcaaaaag aactaaactt    300
gatgatttag ctttgctaga agacttggaa aaacagagag ccttgattaa ggccgaactt    360
gataatgagt taatgaagg aaaggtccag tctggtatgg ggctcatttt gcaaggttat     420
gagtctggct ctgaagaaga gggggaaatt catgaaaagg caagaaatgg aaataggtct    480
agtactagat cttcaagtac aaaggggaaa cttgaacttg tggacaataa aattactaca    540
aagaaacgaa gtaaaagcag atccaaagaa cggactagac ataggtctga taaaaagaaa    600 agtaagggg gtattgaaat cgttaaagag aaaacaacta ggagcaagtc aaaggagagg     660
aaaaaatcta aagcccatc caaagaagt aagtctcaag atcaagcaag gaaatcaaaa      720
tcccctaccc ttagaaggcg atctcaagag aaaattggta aggccagatc tcctactgat    780
gataaggtta aaattgaaga taaaagtaaa tcaaaagata ggaaaaaatc cccaattata    840
aatgaaagta gaagtcgcga tcgaggtaaa aaatccagat ccccagttga tttaagaggt    900
aaatccaaag acagaaggtc acggtccaaa gagagaaaat caaaacggtc tgaaactgat    960
aaagaaaaga agccaattaa atctccctct aaagatgctt catctgggaa agaaaatagg   1020
tcacccagca gaagacctgg tcgtagtcct aaaagaagaa gtttgtctcc aaaaccacgt   1080
gataaatcaa gaagaagcag gtctccactt ttgaatgata agatctaa gcagagcaaa     1140 tccccctcgc ggacactgtc tcctgggaga agagccaaga gccgatcctt agaaagaaaa   1200
cgacgagaac cagagaggag acgactttct tctccaagaa cacgacctcg agatgatatc   1260
ctcagtagac gtgaaagatc aaaagatgcc agccccatca atagatggtc tccaacccga   1320
agaagaagta gatctcccat tagaaggagg tctcgttccc cactcagacg tagcaggtct   1380
ccaagaagaa gaagcagatc tcctcggaga agggacagag tcggaggag cagatcacgc    1440 ttgcgaaggc ggtctcgatc acgcggtggt cgtagacgaa ggagcagaag caaagtaaag   1500
gaagataaat ttaaaggaag tctttctgaa ggaatgaaag ttgagcagga atcttcgtct   1560
gatgataacc ttgaagactt tgatgtagag gaagaagatg aagaagccct aatagaacag   1620
agaagaatcc aaaggcaggc aattgttcag aaatataaat accttgctga agatagcaac   1680
atgtctgtgc catctgaacc aagcagcccc cagagcagta cgagaacacg atcaccatct   1740
ccagatgaca ttctggagcg agtagctgct gatgttaaag agtatgaacg ggaaaatgtt   1800
gatacatttg aggcctcagt gaaagccaag cataatctaa tgacagttga acagaataat   1860
ggttcatctc agaagaagtt gttggcacct gatatgttta cagaatctga tgatatgttt   1920
gctgcgtatt ttgatagtgc tcgtcttcgg gccgctggca ttggaaaaga tttcaaagag   1980
aatcccaacc tcagagataa ctggaccgat gcagaaggct attatcgtgt gaacataggt   2040
gaagtcctag ataaacgtta caatgtgtat ggctacactg ggcaaggtgt attcagtaat   2100
gttgtacgag ccagagataa tgcaagagcc aaccaagaag tggctgtaaa gatcatcaga   2160
aacaatgagc tcatgcaaaa gactggttta aaagaattag agttcttgaa aaacttaat    2220 gatgctgatc ctgatgacaa atttcattgt ctgagactct tcaggcactt ctatcacaag   2280
cagcatcttt gtctggtatt cgagcctctc agcatgaact acgagaggt gttaaaaaaa    2340 tatggtaaag atgttggtct tcatattaaa gctgtaagat cctatagtca gcagttgttc   2400
ctggcattga aactccttaa aagatgcaat atcctacatg cagatatcaa gccagacaat   2460
atcctggtta atgaatccaa aactatttta aagctttgcg attttgggtc ggcttcacat   2520
```

```
gttgcggata atgacataac accttatctt gtcagtagat tttatcgtgc tcctgaaatc    2580
attataggta aaagctatga ctatggtata gatatgtggt ctgtaggttg caccttatac    2640
gaactctata ctggaaaaat tttattccct ggcaaaacca ataaccatat gctgaagctt    2700
gcaatggatc tcaaaggaaa gatgccaaat aagatgattc gaaaggtgt gttcaaagat    2760 cagcattttg atcaaaatct caacttcatg tacatagaag ttgataaagt aacagagagg    2820
gagaaagtta ctgttatgag caccattaat ccaactaagg acctgttggc tgacttgatt    2880
gggtgccaga gacttcctga agaccaacgt aagaaagtac accagctaaa ggacttgttg    2940
gaccagattc tgatgttgga cccagctaaa cgaattagca tcaaccaggc cctacagcac    3000
gccttcatcc aggaaaaaat ttaa                                           3024
```

```
<210> SEQ ID NO 7
<211> LENGTH: 1007
<212> TYPE: PRT
<213> ORGANISM: Homo sapiens

<400> SEQUENCE: 7
```

```
Met Ala Ala Ala Glu Thr Gln Ser Leu Arg Glu Gln Pro Glu Met Glu
1               5                   10                  15

Asp Ala Asn Ser Glu Lys Ser Ile Asn Glu Glu Asn Gly Glu Val Ser
            20                  25                  30

Glu Asp Gln Ser Gln Asn Lys His Ser Arg His Lys Lys Lys Lys His
        35                  40                  45

Lys His Arg Ser Lys His Lys His Lys His Ser Glu Glu Asp
    50                  55                  60

Lys Asp Lys Lys His Lys His Lys His Lys Lys His Lys Arg
65                  70                  75                  80

Lys Glu Val Ile Asp Ala Ser Asp Lys Glu Gly Met Ser Pro Ala Lys
                85                  90                  95

Arg Thr Lys Leu Asp Asp Leu Ala Leu Leu Glu Asp Leu Glu Lys Gln
            100                 105                 110

Arg Ala Leu Ile Lys Ala Glu Leu Asp Asn Glu Leu Met Glu Gly Lys
        115                 120                 125

Val Gln Ser Gly Met Gly Leu Ile Leu Gln Gly Tyr Glu Ser Gly Ser
    130                 135                 140

Glu Glu Glu Gly Glu Ile His Glu Lys Ala Arg Asn Gly Asn Arg Ser
145                 150                 155                 160

Ser Thr Arg Ser Ser Thr Lys Gly Lys Leu Glu Leu Val Asp Asn
                165                 170                 175

Lys Ile Thr Thr Lys Lys Arg Ser Lys Ser Arg Ser Lys Glu Arg Thr
            180                 185                 190

Arg His Arg Ser Asp Lys Lys Ser Lys Gly Gly Ile Glu Ile Val
        195                 200                 205

Lys Glu Lys Thr Thr Arg Ser Lys Lys Glu Arg Lys Lys Ser Lys
    210                 215                 220

Ser Pro Ser Lys Arg Ser Lys Ser Gln Asp Gln Ala Arg Lys Ser Lys
225                 230                 235                 240

Ser Pro Thr Leu Arg Arg Arg Ser Gln Glu Lys Ile Gly Lys Ala Arg
                245                 250                 255

Ser Pro Thr Asp Asp Lys Val Lys Ile Glu Asp Lys Ser Lys Ser Lys
            260                 265                 270

Asp Arg Lys Lys Ser Pro Ile Ile Asn Glu Ser Arg Ser Arg Asp Arg
        275                 280                 285
```

-continued

```
Gly Lys Lys Ser Arg Ser Pro Val Asp Leu Arg Gly Lys Ser Lys Asp
    290                 295                 300

Arg Arg Ser Arg Ser Lys Glu Arg Lys Ser Lys Arg Ser Glu Thr Asp
305                 310                 315                 320

Lys Glu Lys Lys Pro Ile Lys Ser Pro Ser Lys Asp Ala Ser Ser Gly
                325                 330                 335

Lys Glu Asn Arg Ser Pro Ser Arg Arg Pro Gly Arg Ser Pro Lys Arg
            340                 345                 350

Arg Ser Leu Ser Pro Lys Pro Arg Asp Lys Ser Arg Arg Ser Arg Ser
        355                 360                 365

Pro Leu Leu Asn Asp Arg Arg Ser Lys Gln Ser Lys Ser Pro Ser Arg
370                 375                 380

Thr Leu Ser Pro Gly Arg Arg Ala Lys Ser Arg Ser Leu Glu Arg Lys
385                 390                 395                 400

Arg Arg Glu Pro Glu Arg Arg Leu Ser Ser Pro Arg Thr Arg Pro
                405                 410                 415

Arg Asp Asp Ile Leu Ser Arg Glu Arg Ser Lys Asp Ala Ser Pro
                420                 425                 430

Ile Asn Arg Trp Ser Pro Thr Arg Arg Ser Arg Ser Pro Ile Arg
            435                 440                 445

Arg Arg Ser Arg Ser Pro Leu Arg Arg Ser Arg Ser Pro Arg Arg Arg
450                 455                 460

Ser Arg Ser Pro Arg Arg Asp Arg Gly Arg Arg Ser Arg Ser Arg
465                 470                 475                 480

Leu Arg Arg Arg Ser Arg Ser Arg Gly Gly Arg Arg Arg Ser Arg
                485                 490                 495

Ser Lys Val Lys Glu Asp Lys Phe Lys Gly Ser Leu Ser Glu Gly Met
        500                 505                 510

Lys Val Glu Gln Glu Ser Ser Asp Asp Asn Leu Glu Asp Phe Asp
            515                 520                 525

Val Glu Glu Glu Asp Glu Ala Leu Ile Glu Gln Arg Arg Ile Gln
    530                 535                 540

Arg Gln Ala Ile Val Gln Lys Tyr Lys Tyr Leu Ala Glu Asp Ser Asn
545                 550                 555                 560

Met Ser Val Pro Ser Glu Pro Ser Ser Pro Gln Ser Ser Thr Arg Thr
                565                 570                 575

Arg Ser Pro Ser Pro Asp Asp Ile Leu Glu Arg Val Ala Ala Asp Val
            580                 585                 590

Lys Glu Tyr Glu Arg Glu Asn Val Asp Thr Phe Glu Ala Ser Val Lys
        595                 600                 605

Ala Lys His Asn Leu Met Thr Val Glu Gln Asn Asn Gly Ser Ser Gln
610                 615                 620

Lys Lys Leu Leu Ala Pro Asp Met Phe Thr Glu Ser Asp Asp Met Phe
625                 630                 635                 640

Ala Ala Tyr Phe Asp Ser Ala Arg Leu Arg Ala Ala Gly Ile Gly Lys
                645                 650                 655

Asp Phe Lys Glu Asn Pro Asn Leu Arg Asp Asn Trp Thr Asp Ala Glu
            660                 665                 670

Gly Tyr Tyr Arg Val Asn Ile Gly Glu Val Leu Asp Lys Arg Tyr Asn
        675                 680                 685

Val Tyr Gly Tyr Thr Gly Gln Gly Val Phe Ser Asn Val Val Arg Ala
    690                 695                 700

Arg Asp Asn Ala Arg Ala Asn Gln Glu Val Ala Val Lys Ile Ile Arg
```

-continued

```
            705                 710                 715                 720
Asn Asn Glu Leu Met Gln Lys Thr Gly Leu Lys Glu Leu Glu Phe Leu
                    725                 730                 735

Lys Lys Leu Asn Asp Ala Asp Pro Asp Asp Lys Phe His Cys Leu Arg
                740                 745                 750

Leu Phe Arg His Phe Tyr His Lys Gln His Leu Cys Leu Val Phe Glu
            755                 760                 765

Pro Leu Ser Met Asn Leu Arg Glu Val Leu Lys Lys Tyr Gly Lys Asp
        770                 775                 780

Val Gly Leu His Ile Lys Ala Val Arg Ser Tyr Ser Gln Gln Leu Phe
785                 790                 795                 800

Leu Ala Leu Lys Leu Leu Lys Arg Cys Asn Ile Leu His Ala Asp Ile
                805                 810                 815

Lys Pro Asp Asn Ile Leu Val Asn Glu Ser Lys Thr Ile Leu Lys Leu
                820                 825                 830

Cys Asp Phe Gly Ser Ala Ser His Val Ala Asp Asn Asp Ile Thr Pro
            835                 840                 845

Tyr Leu Val Ser Arg Phe Tyr Arg Ala Pro Glu Ile Ile Ile Gly Lys
        850                 855                 860

Ser Tyr Asp Tyr Gly Ile Asp Met Trp Ser Val Gly Cys Thr Leu Tyr
865                 870                 875                 880

Glu Leu Tyr Thr Gly Lys Ile Leu Phe Pro Gly Lys Thr Asn Asn His
                885                 890                 895

Met Leu Lys Leu Ala Met Asp Leu Lys Gly Lys Met Pro Asn Lys Met
                900                 905                 910

Ile Arg Lys Gly Val Phe Lys Asp Gln His Phe Asp Gln Asn Leu Asn
            915                 920                 925

Phe Met Tyr Ile Glu Val Asp Lys Val Thr Glu Arg Glu Lys Val Thr
        930                 935                 940

Val Met Ser Thr Ile Asn Pro Thr Lys Asp Leu Leu Ala Asp Leu Ile
945                 950                 955                 960

Gly Cys Gln Arg Leu Pro Glu Asp Gln Arg Lys Lys Val His Gln Leu
                965                 970                 975

Lys Asp Leu Leu Asp Gln Ile Leu Met Leu Asp Pro Ala Lys Arg Ile
            980                 985                 990

Ser Ile Asn Gln Ala Leu Gln His  Ala Phe Ile Gln Glu  Lys Ile
            995                 1000                1005
```

HPRP4S MODIFIERS OF THE P53 PATHWAY AND METHODS OF USE

REFERENCE TO RELATED APPLICATIONS

This application is a continuation of U.S. patent application Ser. No. 10/211,133, filed Aug. 2, 2002 (now abandoned), which claims priority to U.S. provisional patent application 60/310,362, filed Aug. 6, 2001, and 60/357,501, filed Feb. 15, 2002. The contents of the prior applications are hereby incorporated in their entireties.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855-865; Hollstein, et al., Nucleic Acids Res. (1994) 22:3551-3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi et al., Clin Cancer Res 2000 October; 6(10):4055-63; Koshland, Science (1993) 262:1953).

The human p53 protein normally functions as a central integrator of signals including DNA damage, hypoxia, nucleotide deprivation, and oncogene activation (Prives, Cell (1998) 95:5-8). In response to these signals, p53 protein levels are greatly increased with the result that the accumulated p53 activates cell cycle arrest or apoptosis depending on the nature and strength of these signals. Indeed, multiple lines of experimental evidence have pointed to a key role for p53 as a tumor suppressor (Levine, Cell (1997) 88:323-331). For example, homozygous p53 "knockout" mice are developmentally normal but exhibit nearly 100% incidence of neoplasia in the first year of life (Donehower et al., Nature (1992) 356:215-221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21Waf1/Cip1, cyclin G, Bax, IGF-BP3, and MDM2 (Levine, Cell (1997) 88:323-331).

Mitogen-activated protein kinases (MAPKs) and cyclin-dependent kinases (CDKs) are important proline-directed Ser/Thr kinases that play critical roles in cell differentiation and proliferation. PRP (pre-mRNA processing gene) is a CDK-like kinase with homology to MAPKs (Huang, Y. et al. (2000) Biochem Biophys Res Commun; 271(2): 456-63).

Pre-mRNA processing 4 (PRP4) is a nuclear serine-threonine kinase activated by EGF stimulation, plays a role in transcriptional regulation, and may be involved in pre-mRNA splicing and intracellular signaling (Kojima, T. et al. (2001) J Biol Chem 276, 32247-56; Gross, T. et al. (1997) Nucleic Acids Res. 25: 1028-1035). The Prp4 gene of *Schizosaccharomyces pombe* encodes a protein kinase that appears to be involved in pre-mRNA splicing (Gross et al., supra). The sequence of PRP4 kinase and its function in pre-mRNA splicing are highly conserved in yeast and humans (Wang, et al., Hum Mol Genet. (1997) November; 6(12):2117-26; Schwelnus et al., EMBO Rep. (2001) January; 2(1):35-41). Based on kinase domain sequence, Prp4 belongs to the Clk (CDC-like kinase) family and interacts with CLK1 (Kojima et al., supra).

The ability to manipulate the genomes of model organisms such as *C. elegans* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Dulubova I, et al, J Neurochem 2001 April; 77(1):229-38; Cai T, et al., Diabetologia 2001 January; 44(1):81-8; Pasquinelli A E, et al., Nature. 2000 Nov. 2; 408(6808):37-8; Ivanov I P, et al., EMBO J 2000 Apr. 17; 19(8):1907-17; Vajo Z et al., Mamm Genome 1999 October; 10(10):1000-4). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p53, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p53 pathway in *C. elagans*, and identified their human orthologs, hereinafter referred to as hPRP4. The invention provides methods for utilizing these p53 modifier genes and polypeptides to identify hPRP4-modulating agents that are candidate therapeutic agents that can be used in the treatment of disorders associated with defective or impaired p53 function and/or hPRP4 function. Preferred hPRP4-modulating agents specifically bind to hPRP4 polypeptides and restore p53 function. Other preferred hPRP4-modulating agents are nucleic acid modulators such as antisense oligomers and RNAi that repress hPRP4 gene expression or product activity by, for example, binding to and inhibiting the respective nucleic acid (i.e. DNA or mRNA).

hPRP4 modulating agents may be evaluated by any convenient in vitro or in vivo assay for molecular interaction with an hPRP4 polypeptide or nucleic acid. In one embodiment, candidate hPRP4 modulating agents are tested with an assay system comprising a hPRP4 polypeptide or nucleic acid. Agents that produce a change in the activity of the assay system relative to controls are identified as candidate p53 modulating agents. The assay system may be cell-based or cell-free. hPRP4-modulating agents include hPRP4 related proteins (e.g. dominant negative mutants, and biotherapeutics); hPRP4-specific antibodies; hPRP4-specific antisense oligomers and other nucleic acid modulators; and chemical agents that specifically bind to or interact with hPRP4 or compete with hPRP4 binding partner (e.g. by binding to an hPRP4 binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate p53 pathway modulating agents are further tested using a second assay system that detects changes in the p53 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 pathway, such as an angiogenic, apoptotic, or cell proliferation disorder (e.g. cancer).

The invention further provides methods for modulating the hPRP4 function and/or the p53 pathway in a mammalian cell by contacting the mammalian cell with an agent that specifically binds a hPRP4 polypeptide or nucleic acid. The agent may be a small molecule modulator, a nucleic acid modulator, or an antibody and may be administered to a mammalian animal predetermined to have a pathology associated the p53 pathway.

DETAILED DESCRIPTION OF THE INVENTION

Genetic screens were designed to identify modifiers of the p53 pathway in *C. elagans*, where a homozygous p53 deletion mutant was used. Various specific genes were silenced by RNA inhibition (RNAi). Methods for using RNAi to silence genes in *C. elegans* are known in the art (Fire A, et al., 1998 Nature 391:806-811; Fire, A. Trends Genet. 15, 358-363 (1999); WO9932619). Genes causing altered phenotypes in the worms were identified as modifiers of the p53 pathway. Modifiers of particular interest, F22D6.5, were identified followed by identification of their human orthologs.

In vitro and in vivo methods of assessing hPRP4 function are provided herein. Modulation of the hPRP4 or their respective binding partners is useful for understanding the association of the p53 pathway and its members in normal and disease conditions and for developing diagnostics and therapeutic modalities for p53 related pathologies. hPRP4-modulating agents that act by inhibiting or enhancing hPRP4 expression, directly or indirectly, for example, by affecting an hPRP4 function such as enzymatic (e.g., catalytic) or binding activity, can be identified using methods provided herein. hPRP4 modulating agents are useful in diagnosis, therapy and pharmaceutical development.

Nucleic Acids and Polypeptides of the Invention

Sequences related to hPRP4 nucleic acids and polypeptides that can be used in the invention are disclosed in Genbank (referenced by Genbank identifier (GI) number) as GI#s 14571505 (SEQ ID NO:1), 17999534 (SEQ ID NO:2), 14746978 (SEQ ID NO:3), 14714402 (SEQ ID NO:4), and 1399461 (SEQ ID NO:5) for nucleic acid, and GI#14571506 (SEQ ID NO:7) for polypeptides. Additionally, sequences of clone N5A08 (SEQ ID NO:6) can be used in the methods of the invention.

hPRP4s are nuclear serine/threonine kinase proteins with kinase domains. The term "hPRP4 polypeptide" refers to a full-length hPRP4 protein or a functionally active fragment or derivative thereof. A "functionally active" hPRP4 fragment or derivative exhibits one or more functional activities associated with a full-length, wild-type hPRP4 protein, such as antigenic or immunogenic activity, enzymatic activity, ability to bind natural cellular substrates, etc. The functional activity of hPRP4 proteins, derivatives and fragments can be assayed by various methods known to one skilled in the art (Current Protocols in Protein Science (1998) Coligan et al., eds., John Wiley & Sons, Inc., Somerset, N.J.) and as further discussed below. For purposes herein, functionally active fragments also include those fragments that comprise one or more structural domains of an hPRP4, such as a kinase domain or a binding domain. Protein domains can be identified using the PFAM program (Bateman A., et al., Nucleic Acids Res, 1999, 27:260-2). For example, the kinase domain of hPRP4 from GI#14571506 (SEQ ID NO:7) is located at approximately amino acid residues 687-1003 (PFAM 00069). Methods for obtaining hPRP4 polypeptides are also further described below. In some embodiments, preferred fragments are functionally active, domain-containing fragments comprising at least 25 contiguous amino acids, preferably at least 50, more preferably 75, and most preferably at least 100 contiguous amino acids of SEQ ID NO:7 (an hPRP4). In further preferred embodiments, the fragment comprises the entire kinase (functionally active) domain.

The term "hPRP4 nucleic acid" refers to a DNA or RNA molecule that encodes a hPRP4 polypeptide. Preferably, the hPRP4 polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with hPRP4. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *C. elegans*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs:1, 2, 3, 4, 5, or 6. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1, 2, 3, 4, 5, or 6 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% FICOLL®, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of hPRP4 Nucleic Acids and Polypeptides hPRP4 nucleic acids and polypeptides, useful for identifying and testing agents that modulate hPRP4 function and for other applications related to the involvement of hPRP4 in the p53 pathway. hPRP4 nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an hPRP4 protein for assays used to assess hPRP4 function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant hPRP4 is expressed in a cell line known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). The recombinant cells are used in cell-based screening assay systems of the invention, as described further below.

The nucleotide sequence encoding an hPRP4 polypeptide can be inserted into any appropriate expression vector. The necessary transcriptional and translational signals, including promoter/enhancer element, can derive from the native hPRP4 gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the hPRP4 gene product, the expression vector can comprise a promoter operably linked to an hPRP4 gene nucleic acid, one or more origins of replication, and, one or more selectable markers (e.g. thymidine kinase activity, resistance to antibiotics, etc.). Alternatively, recombinant expression vectors can be identified by assaying for the expression of the hPRP4 gene product based on the physical or functional properties of the hPRP4 protein in in vitro assay systems (e.g. immunoassays).

The hPRP4 protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the hPRP4 gene sequence is identified, the gene product can be isolated and purified using standard methods (e.g. ion exchange, affinity, and gel exclusion chromatography; centrifugation; differential solubility; electrophoresis). Alternatively, native hPRP4 proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of hPRP4 or other genes associated with the p53 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter hPRP4 expression may be used in in vivo assays to test for activity of a candidate p53 modulating agent, or to further assess the role of hPRP4 in a p53 pathway process such as apoptosis or cell proliferation. Preferably, the altered hPRP4 expression results in a detectable phenotype, such as decreased or increased levels of cell proliferation, angiogenesis, or apoptosis compared to control animals having normal hPRP4 expression. The genetically modified animal may additionally have altered p53 expression (e.g. p53 knockout). Preferred genetically modified animals are mammals such as primates, rodents (preferably mice), cows, horses, goats, sheep, pigs, dogs and cats. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous hPRP4 gene that results in a decrease of hPRP4 function, preferably such that hPRP4 expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse hPRP4 gene is used to construct a homologous recombination vector suitable for altering an endogenous hPRP4 gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the hPRP4 gene, e.g., by introduction of additional copies of hPRP4, or by operatively inserting a regulatory sequence that provides for altered expression of an endogenous copy of the hPRP4 gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the p53 pathway, as animal models of disease and disorders implicating defective p53 function, and for in vivo testing of candidate therapeutic agents, such as those identified in screens described below. The candidate therapeutic agents are administered to a genetically modified animal having altered hPRP4 function and phenotypic changes are compared with appropriate control animals such as genetically modified animals that receive placebo treatment, and/or animals with unaltered hPRP4 expression that receive candidate therapeutic agent.

In addition to the above-described genetically modified animals having altered hPRP4 function, animal models having defective p53 function (and otherwise normal hPRP4 function), can be used in the methods of the present invention. For example, a p53 knockout mouse can be used to assess, in vivo, the activity of a candidate p53 modulating agent identified in one of the in vitro assays described below. p53 knockout mice are described in the literature (Jacks et al., Nature 2001; 410:1111-1116, 1043-1044; Donehower et al., supra). Preferably, the candidate p53 modulating agent when administered to a model system with cells defective in p53 function, produces a detectable phenotypic change in the model system indicating that the p53 function is restored, i.e., the cells exhibit normal cell cycle progression.

Modulating Agents

The invention provides methods to identify agents that interact with and/or modulate the function of hPRP4 and/or the p53 pathway. Modulating agents identified by the methods are also part of the invention. Such agents are useful in a variety of diagnostic and therapeutic applications associated with the p53 pathway, as well as in further analysis of the hPRP4 protein and its contribution to the p53 pathway. Accordingly, the invention also provides methods for modulating the p53 pathway comprising the step of specifically modulating hPRP4 activity by administering a hPRP4-interacting or -modulating agent.

As used herein, an "hPRP4-modulating agent" is any agent that modulated hPRP4 function, for example, an agent that interacts with hPRP4 to inhibit or enhance hPRP4 activity or otherwise affect normal hPRP4 function. hPRP4 function can be affected at any level, including transcription, protein expression, protein localization, and cellular or extra-cellular activity. In a preferred embodiment, the hPRP4-modulating agent specifically modulates the function of the hPRP4. The phrases "specific modulating agent", "specifically modulates", etc., are used herein to refer to modulating agents that directly bind to the hPRP4 polypeptide or nucleic acid, and preferably inhibit, enhance, or otherwise alter, the function of the hPRP4. These phrases also encompasses modulating agents that alter the interaction of the hPRP4 with a binding partner, substrate, or cofactor (e.g. by binding to a binding partner of an hPRP4, or to a protein/binding partner complex, and altering hPRP4 function). In a further preferred embodiment, the hPRP4-modulating agent is a modulator of the p53 pathway (e.g. it restores and/or upregulates p53 function) and thus is also a p53-modulating agent.

Preferred hPRP4-modulating agents include small molecule compounds; hPRP4-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules, are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the hPRP4 protein or may be identified by screening compound libraries. Alternative appropriate modulators of this class are natural products, particularly secondary metabolites from organisms such as plants or fungi, which can also be identified by screening compound libraries for hPRP4-modulating activity. Methods for generating and obtaining compounds are well known in the art (Schreiber S L, Science (2000) 151:1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the p53 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific hPRP4-interacting proteins are useful in a variety of diagnostic and therapeutic applications related to the p53 pathway and related disorders, as well as in validation assays for other hPRP4-modulating agents. In a preferred embodiment, hPRP4-interacting proteins affect normal hPRP4 function, including transcription, protein expression, protein localization, and cellular or extra-cellular activity. In another embodiment, hPRP4-interacting proteins are useful in detecting and providing information about the function of hPRP4 proteins, as is relevant to p53 related disorders, such as cancer (e.g., for diagnostic means).

An hPRP4-interacting protein may be endogenous, i.e. one that naturally interacts genetically or biochemically with an hPRP4, such as a member of the hPRP4 pathway that modulates hPRP4 expression, localization, and/or activity. hPRP4-modulators include dominant negative forms of hPRP4-interacting proteins and of hPRP4 proteins themselves. Yeast two-hybrid and variant screens offer preferred methods for identifying endogenous hPRP4-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An hPRP4-interacting protein may be an exogenous protein, such as an hPRP4-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). hPRP4 antibodies are further discussed below.

In preferred embodiments, an hPRP4-interacting protein specifically binds an hPRP4 protein. In alternative preferred embodiments, an hPRP4-modulating agent binds an hPRP4 substrate, binding partner, or cofactor.

Antibodies

In another embodiment, the protein modulator is an hPRP4 specific antibody agonist or antagonist. The antibodies have therapeutic and diagnostic utilities, and can be used in screening assays to identify hPRP4 modulators. The antibodies can also be used in dissecting the portions of the hPRP4 pathway responsible for various cellular responses and in the general processing and maturation of the hPRP4.

Antibodies that specifically bind hPRP4 polypeptides can be generated using known methods. Preferably the antibody is specific to a mammalian ortholog of hPRP4 polypeptide, and more preferably, to human hPRP4. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of hPRP4 which are particularly antigenic can be selected, for example, by routine screening of hPRP4 polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence shown in SEQ ID NO:7. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of hPRP4 or substantially purified fragments thereof. If hPRP4 fragments are used, they preferably comprise at least 10, and more preferably, at least 20 contiguous amino acids of an hPRP4 protein. In a particular embodiment, hPRP4-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of hPRP4-specific antibodies is assayed by an appropriate assay such as a solid phase enzyme-linked immunosorbant assay (ELISA) using immobilized corresponding hPRP4 polypeptides. Other assays, such as radioimmunoassays or fluorescent assays might also be used.

Chimeric antibodies specific to hPRP4 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

hPRP4-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred hPRP4-modulating agents comprise nucleic acid molecules, such as antisense oligomers or double stranded RNA (dsRNA), which generally inhibit hPRP4 activity. Preferred nucleic acid modulators interfere with the function of the hPRP4 nucleic acid such as DNA replication, transcription, translocation of the hPRP4 RNA to the site of protein translation, translation of protein from the hPRP4 RNA, splicing of the hPRP4 RNA to yield one or more mRNA species, or catalytic activity which may be engaged in or facilitated by the hPRP4 RNA.

In one embodiment, the antisense oligomer is an oligonucleotide that is sufficiently complementary to an hPRP4 mRNA to bind to and prevent translation, preferably by binding to the 5' untranslated region. hPRP4-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev. :7:187-95; U.S. Pat. No. 5,235,033; and U.S. Pat. No. 5,378,841).

Alternative preferred hPRP4 nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elagans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, an hPRP4-specific nucleic acid modulator is used in an assay to further elucidate the role of the hPRP4 in the p53 pathway, and/or its relationship to other members of the pathway. In another aspect of the invention, an hPRP4-specific antisense oligomer is used as a therapeutic agent for treatment of p53-related disease states.

Assay Systems

The invention provides assay systems and screening methods for identifying specific modulators of hPRP4 activity. As used herein, an "assay system" encompasses all the components required for performing and analyzing results of an assay that detects and/or measures a particular event. In general, primary assays are used to identify or confirm a modulator's specific biochemical or molecular effect with respect to the hPRP4 nucleic acid or protein. In general, secondary assays further assess the activity of a hPRP4 modulating agent identified by a primary assay and may confirm that the modulating agent affects hPRP4 in a manner relevant to the p53 pathway. In some cases, hPRP4 modulators will be directly tested in a secondary assay.

In a preferred embodiment, the screening method comprises contacting a suitable assay system comprising an hPRP4 polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates hPRP4 activity, and hence the p53 pathway. The hPRP4 polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of hPRP4 and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when hPRP4-interacting proteins are used in screens to identify small molecule modulators, the binding specificity of the interacting protein to the hPRP4 protein may be assayed by various known methods such as substrate processing (e.g. ability of the candidate hPRP4-specific binding agents to function as negative effectors in hPRP4-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit hPRP4 specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a hPRP4 polypeptide, a fusion protein thereof, or to cells or membranes bearing the polypeptide or fusion protein. The hPRP4 polypeptide can be full length or a fragment thereof that retains functional hPRP4 activity. The hPRP4 polypeptide may be fused to another polypeptide, such as a peptide tag for detection or anchoring, or to another tag. The hPRP4 polypeptide is preferably human hPRP4, or is an ortholog or derivative thereof as described above. In a preferred embodiment, the screening assay detects candidate agent-based modulation of hPRP4 interaction with a binding target, such as an endogenous or exogenous protein or other substrate that has hPRP4-specific binding activity, and can be used to assess normal hPRP4 gene function.

Suitable assay formats that may be adapted to screen for hPRP4 modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 011:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate hPRP4 and p53 pathway modulators (e.g. U.S. Pat. No. 6,165,992 (kinase assays); U.S. Pat. Nos. 5,550,019 and 6,133,437 (apoptosis assays); U.S. Pat. No. 6,020,135 (p53 modulation), among others). Specific preferred assays are described in more detail below.

Kinase assays. In some preferred embodiments the screening assay detects the ability of the test agent to modulate the kinase activity of an hPRP4 polypeptide. In further embodiments, a cell-free kinase assay system is used to identify a candidate p53 modulating agent, and a secondary, cell-based assay, such as an apoptosis or hypoxic induction assay (described below), may be used to further characterize the candidate p53 modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). An apoptosis assay system may comprise a cell that expresses an hPRP4, and that optionally has defective p53 function (e.g. p53 is over-expressed or under-expressed relative to wild-type cells). A test agent can be added to the apoptosis assay system and changes in induction of apoptosis relative to controls where no test agent is added, identify candidate p53 modulating agents. In some embodiments of the invention, an apoptosis assay may be used as a secondary assay to test a candidate p53 modulating agents that is initially identified using a cell-free assay system. An apoptosis assay may also be used to test whether hPRP4 function plays a direct role in apoptosis. For example, an apoptosis assay may be performed on cells that over- or under-express hPRP4 relative to wild type cells. Differences in apoptotic response compared to wild type cells suggests that the hPRP4 plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter).

Cell proliferation may also be assayed by colony formation in soft agar (Sambrook et al., Molecular Cloning, Cold Spring Harbor (1989)). For example, cells transformed with hPRP4 are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237-55). Cells transfected with an hPRP4 may be stained with propidium iodide and evaluated in a flow cytometer (available from Becton Dickinson).

Accordingly, a cell proliferation or cell cycle assay system may comprise a cell that expresses an hPRP4, and that optionally has defective p53 function (e.g. p53 is over-expressed or under-expressed relative to wild-type cells). A test agent can be added to the assay system and changes in cell proliferation or cell cycle relative to controls where no test agent is added, identify candidate p53 modulating agents. In some embodiments of the invention, the cell proliferation or cell cycle assay may be used as a secondary assay to test a candidate p53 modulating agents that is initially identified using another assay system such as a cell-free kinase assay system. A cell proliferation assay may also be used to test whether hPRP4 function plays a direct role in cell proliferation or cell cycle. For example, a cell proliferation or cell cycle assay may be performed on cells that over- or under-express hPRP4 relative to wild type cells. Differences in proliferation or cell cycle compared to wild type cells suggests that the hPRP4 plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses an hPRP4, and that optionally has defective p53 function (e.g. p53 is over-expressed or under-expressed relative to wild-type cells). A test agent can be added to the angiogenesis assay system and changes in angiogenesis relative to controls where no test agent is added, identify candidate p53 modulating agents. In some embodiments of the invention, the angiogenesis assay may be used as a secondary assay to test a candidate p53 modulating agent that is initially identified using another assay system. An angiogenesis assay may also be used to test whether hPRP4 function plays a direct role in cell proliferation. For example, an angiogenesis assay may be performed on cells that over- or under-express hPRP4 relative to wild type cells. Differences in angiogenesis compared to wild type cells suggest that the hPRP4 plays a direct role in angiogenesis.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with hPRP4 in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses an hPRP4, and that optionally has a mutated p53 (e.g. p53 is over-expressed or under-expressed relative to wild-type cells). A test agent can be added to the hypoxic induction assay system and changes in hypoxic response relative to controls where no test agent is added, identify candidate p53 modulating agents. In some embodiments of the invention, the hypoxic induction assay may be used as a secondary assay to test a candidate p53 modulating agent that is initially identified using another assay system. A hypoxic induction assay may also be used to test whether hPRP4 function plays a direct role in the hypoxic response. For example, a hypoxic induction assay may be performed on cells that over- or under-express hPRP4 relative to wild type cells. Differences in hypoxic response compared to wild type cells suggest that the hPRP4 plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Cell Migration. An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing an hPRP4's response to a variety of pro-angiogenic factors, including tumor angiogenic and inflammatory angiogenic agents, and culturing the cells in serum free medium.

Sprouting assay. A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143:1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the hPRP4 protein. Methods for testing antibody affinity and specificity are well known in the art (Harlow and Lane, 1988, 1999, supra). The enzyme-linked immunosorbant assay (ELISA) is a preferred method for detecting hPRP4-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance hPRP4 gene expression, preferably mRNA expression. In general, expression analysis comprises comparing hPRP4 expression in like populations of cells (e.g., two pools of cells that endogenously or recombinantly express hPRP4) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS®), or microarray analysis may be used to confirm that hPRP4 mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the hPRP4 protein or specific peptides. A variety of means including Western blotting, ELISA, or in situ detection, are available (Harlow E and Lane D, 1988 and 1999, supra).

Secondary Assays

Secondary assays may be used to further assess the activity of hPRP4-modulating agent identified by any of the above methods to confirm that the modulating agent affects hPRP4 in a manner relevant to the p53 pathway. As used herein, hPRP4-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with hPRP4.

Secondary assays generally compare like populations of cells or animals (e.g., two pools of cells or animals that endogenously or recombinantly express hPRP4) in the presence and absence of the candidate modulator. In general, such assays test whether treatment of cells or animals with a candidate hPRP4-modulating agent results in changes in the p53 pathway in comparison to untreated (or mock- or placebo-treated) cells or animals. Certain assays use "sensitized genetic backgrounds", which, as used herein, describe cells or animals engineered for altered expression of genes in the p53 or interacting pathways.

Cell-Based Assays

Cell based assays may use a variety of mammalian cell lines known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). Cell based assays may detect endogenous p53 pathway activity or may rely on recombinant expression of p53 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 pathway may be used to test candidate hPRP4 modulators. Models for defective p53 pathway typically use genetically modified animals that have been engineered to mis-express (e.g., over-express or lack expression in) genes involved in the p53 pathway. Assays generally require systemic delivery of the candidate modulators, such as by oral administration, injection, etc.

In a preferred embodiment, p53 pathway activity is assessed by monitoring neovascularization and angiogenesis. Animal models with defective and normal p53 are used to test the candidate modulator's effect on hPRP4 in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which overexpress the hPRP4. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on hPRP4 is assessed via tumorigenicity assays. In one example, xenograft human tumors are implanted SC into female athymic mice, 6-7 week old, as single cell suspensions either from a pre-existing tumor or from in vitro culture. The tumors which express the hPRP4 endogenously are injected in the flank, $1 \times 10^5$ to $1 \times 10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

Diagnostic and Therapeutic Uses

Specific hPRP4-modulating agents are useful in a variety of diagnostic and therapeutic applications where disease or disease prognosis is related to defects in the p53 pathway, such as angiogenic, apoptotic, or cell proliferation disorders. Accordingly, the invention also provides methods for modulating the p53 pathway in a cell, preferably a cell pre-determined to have defective or impaired p53 function (e.g. due to overexpression, underexpression, or misexpression of p53, or due to gene mutations), comprising the step of administering an agent to the cell that specifically modulates hPRP4 activity. Preferably, the modulating agent produces a detectable phenotypic change in the cell indicating that the p53 function is restored. The phrase "function is restored", and equivalents, as used herein, means that the desired phenotype is achieved, or is brought closer to normal compared to untreated cells. For example, with restored p53 function, cell proliferation and/or progression through cell cycle may normalize, or be brought closer to normal relative to untreated cells. The invention also provides methods for treating disorders or disease associated with impaired p53 function by administering a therapeutically effective amount of an hPRP4-modulating agent that modulates the p53 pathway. The invention further provides methods for modulating hPRP4 function in a cell, preferably a cell pre-determined to have defective or impaired hPRP4 function, by administering an hPRP4-modulating agent. Additionally, the invention provides a method for treating disorders or disease associated with impaired hPRP4 function by administering a therapeutically effective amount of an hPRP4-modulating agent.

The discovery that hPRP4 is implicated in p53 pathway provides for a variety of methods that can be employed for the diagnostic and prognostic evaluation of diseases and disorders involving defects in the p53 pathway and for the identification of subjects having a predisposition to such diseases and disorders.

Various expression analysis methods can be used to diagnose whether hPRP4 expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective p53 signaling that express an hPRP4, are identified as amenable to treatment with an hPRP4 modulating agent. In a preferred application, the p53 defective tissue overexpresses an hPRP4 relative to normal tissue. For example, a Northern blot analysis of mRNA from tumor and normal cell lines, or from tumor and matching normal tissue samples from the same patient, using full or partial hPRP4 cDNA sequences as probes, can determine whether particular tumors express or overexpress hPRP4. Alternatively, the TAQMAN® is used for quantitative RT-PCR analysis of hPRP4 expression in cell lines, normal tissues and tumor samples (PE APPLIED BIOSYSTEMS®).

Various other diagnostic methods may be performed, for example, utilizing reagents such as the hPRP4 oligonucleotides, and antibodies directed against an hPRP4, as described above for: (1) the detection of the presence of hPRP4 gene mutations, or the detection of either over- or under-expression of hPRP4 mRNA relative to the non-disorder state; (2) the detection of either an over- or an under-abundance of hPRP4 gene product relative to the non-disorder state; and (3) the detection of perturbations or abnormalities in the signal transduction pathway mediated by hPRP4.

Thus, in a specific embodiment, the invention is drawn to a method for diagnosing a disease or disorder in a patient that is associated with alterations in hPRP4 expression, the method comprising: a) obtaining a biological sample from the patient; b) contacting the sample with a probe for hPRP4 expression; c) comparing results from step (b) with a control; and d) determining whether step (c) indicates a likelihood of the disease or disorder. Preferably, the disease is cancer, most preferably ovarian cancer. The probe may be either DNA or protein, including an antibody.

EXAMPLES

The following experimental section and examples are offered by way of illustration and not by way of limitation.

I. *C. elagans* p53 Screen

A systematic RNAi of various genes was carried out in worms homozygous for p53 deletion. p53 (−/−) worms have a normal phenotype, but are defective in germline apoptotic response to ionizing radiation as p53 is involved in the DNA damage response. After silencing of each gene by RNAi, worms were subject to gamma-irradiation, and phenotypes were scored. The worm F22D6.5 suppressed the p53 block in DNA-damage induced apoptosis in germline.

BLAST analysis (Altschul et al., supra) was employed to identify Targets from *C. elegans* modifiers. For example, representative sequence from hPRP4, GI#14571506 (SEQ ID NO:7), shares 40% amino acid identity with the *C. elegans* F22D6.5.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10(11):1679-89) programs. For example, the kinase domain of hPRP4 from GI#14571506 (SEQ ID NO:7) is located at approximately amino acid residues 687-1003 (PFAM 00069).

II. High-Throughput In Vitro Fluorescence Polarization Assay

Fluorescently-labeled hPRP4 peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of hPRP4 activity.

III. High-Throughput In Vitro Binding Assay.

$^{33}$P-labeled hPRP4 peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 modulating agents.

IV. Immunoprecipitations and Immunoblotting

For coprecipitation of transfected proteins, 3×10$^6$ appropriate recombinant cells containing the hPRP4 proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified hPRP4 is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation (Mg2$^+$ or Mn$^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC$^{SM}$ (American Type Culture Collection, Manassas, Va. 20110-2209). Normal and tumor tissues were obtained from Impath, U C Davis, CLONTECH™, STRATAGENE®, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product.

TAQMAN® reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

hPRP4 (GI#14571505, SEQ ID NO: 1) was overexpressed in 2 of 7 ovarian tumors. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

What is claimed is:

1. A method of identifying an apoptosis modulating agent in a p53 defective cell, said method comprising the steps of:
  (a) providing a p53 defective cell comprising a purified human pre-mRNA processing 4 (hPRP4) nucleic acid encoding the polypeptide of SEQ ID NO: 7 or a functionally active fragment or derivative thereof, wherein the functionally active fragment or derivative has kinase activity;
  (b) contacting the p53 defective cell with a test agent; and
  (c) detecting the expression of hPRP4 in the p53 defective cell, wherein a difference between the expression of hPRP4 in the presence of the test agent compared to its absence identifies the test agent as an apoptosis modulating agent.

2. The method of claim 1, wherein the test agent is a nucleic acid modulator targeted against hPRP4.

3. The method of claim 2, wherein the nucleic acid modulator is an antisense oligomer.

4. The method of claim 2, wherein the nucleic acid modulator is a phosphothioate morpholino oligomer (PM0).

5. The method of claim 2, wherein the nucleic acid modulator is an siRNA.

6. A method of identifying an agent that modulates cell proliferation in a p53 defective cell, said method comprising the steps of:
  (a) providing a p53 defective cell comprising a purified human pre-mRNA processing 4 (hPRP4) nucleic acid encoding the polypeptide of SEQ ID NO: 7 or a functionally active fragment or derivative thereof, wherein the functionally active fragment or derivative has kinase activity;
  (b) contacting the p53 defective cell with a test agent; and
  (c) detecting the expression of hPRP4 in the p53 defective cell, wherein a difference between the expression of hPRP4 in the presence of the test agent compared to its absence identifies the test agent as an agent that modulates cell proliferation.

7. The method of claim 6, wherein the test agent is a nucleic acid modulator targeted against hPRP4.

8. The method of claim 7, wherein the nucleic acid modulator is an antisense oligomer.

9. The method of claim 7, wherein the nucleic acid modulator is a phosphothioate morpholino oligomer (PM0).

10. The method of claim 7, wherein the nucleic acid modulator is an siRNA.

* * * * *